(12) United States Patent
Itkowitz et al.

(10) Patent No.: US 12,714,522 B2
(45) **Date of Patent: *Aug. 25, 2026**

(54) STRUCTURAL ADJUSTMENT SYSTEMS AND METHODS FOR A TELEOPERATIONAL MEDICAL SYSTEM

(71) Applicant: INTUITIVE SURGICAL OPERATIONS, INC., Sunnyvale, CA (US)

(72) Inventors: Brandon D. Itkowitz, San Jose, CA (US); Paul W. Mohr, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 138 days.

This patent is subject to a terminal disclaimer.

(21) Appl. No.: 18/609,994

(22) Filed: Mar. 19, 2024

(65) Prior Publication Data

US 2024/0216090 A1 Jul. 4, 2024

Related U.S. Application Data

(63) Continuation of application No. 17/870,528, filed on Jul. 21, 2022, now Pat. No. 11,963,731, which is a (Continued)

(51) Int. Cl.
*A61B 34/30* (2016.01)
*A61B 34/35* (2016.01)
(Continued)

(52) U.S. Cl.
CPC .............. *A61B 34/35* (2016.02); *A61B 34/30* (2016.02); *A61B 34/37* (2016.02); *A61B 90/03* (2016.02); *B25J 9/1689* (2013.01)

(58) Field of Classification Search
CPC ........ A61B 34/30; A61B 34/70; B25J 9/1689; B25J 9/1664; B25J 13/089; B25J 9/1666;
(Continued)

(56) References Cited

U.S. PATENT DOCUMENTS 8,004,229 B2 8/2011 Nowlin et al.
8,160,743 B2 4/2012 Birkenbach et al.
(Continued)

FOREIGN PATENT DOCUMENTS

CN 102596084 A 7/2012
WO WO-2010151438 A1 12/2010
(Continued)

OTHER PUBLICATIONS

Extended European Search Report for Application No. EP15765367.6, mailed on Nov. 9, 2017, 9 pages.
(Continued)

*Primary Examiner* — Khoi H Tran
*Assistant Examiner* — Tanner L Cullen
(74) *Attorney, Agent, or Firm* — Haynes & Boone, LLP.

(57) ABSTRACT

A system comprises a sensing means for sensing an arrangement of a manipulator assembly. The system further comprises a control means for: determining a motion limit of the manipulator assembly based on the sensed arrangement; and selecting a threshold limit from a plurality of pre-stored threshold limits based on which procedure type is to be performed with the manipulator assembly. The selected threshold limit is associated with a procedure type and defines a limit of a range to be potentially travelled by the manipulator assembly to perform a procedure. The control means are further for: comparing the motion limit to the selected threshold limit to determine whether the selected threshold limit is outside a range of motion bounded by the motion limit; and providing a notification indicative of
(Continued)

whether the selected threshold limit is outside the range of motion bounded by the motion limit.

20 Claims, 10 Drawing Sheets

Related U.S. Application Data continuation of application No. 16/214,623, filed on Dec. 10, 2018, now Pat. No. 11,432,893, which is a continuation of application No. 15/262,780, filed as application No. PCT/US2015/018456 on Mar. 3, 2015, now Pat. No. 10,182,873.

(60) Provisional application No. 61/954,090, filed on Mar. 17, 2014.

(51) Int. Cl.
*A61B 34/37* (2016.01)
*A61B 90/00* (2016.01)
*B25J 9/16* (2006.01)

(58) Field of Classification Search
CPC ...... B25J 9/1676; B25J 9/1633; B25J 9/1612; G08B 3/10; G08B 5/22; G08B 21/182
See application file for complete search history.

(56) References Cited

U.S. PATENT DOCUMENTS 8,282,653 B2 10/2012 Nelson et al.
8,506,555 B2 8/2013 Ruiz Morales
8,886,331 B2 11/2014 Labadie et al.
10,182,873 B2 1/2019 Itkowitz et al.
11,432,893 B2 9/2022 Itkowitz et al.
11,963,731 B2 4/2024 Itkowitz et al.
2004/0243147 A1 12/2004 Lipow
2007/0142825 A1 6/2007 Prisco et al.
2008/0161829 A1* 7/2008 Kang ..................... B25J 9/0042 606/130
2008/0221731 A1* 9/2008 Wang ..................... A61B 34/35 901/14
2009/0228145 A1 9/2009 Hodgson et al.
2009/0326318 A1 12/2009 Tognaccini et al.
2011/0054308 A1 3/2011 Cohen et al.
2011/0238082 A1 9/2011 Wenderow et al.
2012/0323247 A1* 12/2012 Bettenga ................... A61F 2/46 606/91
2016/0339586 A1* 11/2016 Komuro ............... A61B 1/0016
2016/0346924 A1* 12/2016 Hasegawa .............. B25J 9/1612
2022/0401167 A1 12/2022 Itkowitz et al.

FOREIGN PATENT DOCUMENTS

WO WO-2011149260 A2 12/2011
WO WO-2016009301 A2 1/2016

OTHER PUBLICATIONS

Extended European Search Report for Application No. EP22151060.5, mailed on Apr. 20, 2022, 8 pages.
International Search Report and Written Opinion for Application No. PCT/US15/18456, mailed on May 21, 2015, 10 pages.
Vertut, J., and Coiffet, P., “Robot Technology: Teleoperation and Robotics Evolution and Development,” English translation, Prentice-Hall, Inc., Inglewood Cliffs, NJ, USA 1986, vol. 3A, 332 pages.

* cited by examiner

STRUCTURAL ADJUSTMENT SYSTEMS AND METHODS FOR A TELEOPERATIONAL MEDICAL SYSTEM

CROSS-REFERENCE TO RELATED APPLICATIONS

This patent application is a continuation of U.S. patent application Ser. No. 17/870,528, filed Jul. 21, 2022, which is a continuation of U.S. patent application Ser. No. 16/214,623, filed Dec. 10, 2018, now U.S. Pat. No. 11,432,893, which is a continuation of U.S. patent application Ser. No. 15/262,780, filed Sep. 12, 2016, now U.S. Pat. No. 10,182,873, which is the U.S. national phase of International Application No. PCT/US2015/018456, filed Mar. 3, 2015, which designated the U.S. and claims priority to and the benefit of the filing date of U.S. Provisional Patent Application No. 61/954,090, filed Mar. 17, 2014, all of which are incorporated by reference herein in their entirety.

FIELD

The present disclosure is directed to systems and methods for controlling a teleoperational medical system and more particularly to systems and methods for improving a structural arrangement of the teleoperational medical system for a surgical procedure.

BACKGROUND

Surgical procedures can be performed using a teleoperational medical system in a minimally invasive manner. The benefits of a minimally invasive surgery are well known and include less patient trauma, less blood loss, and faster recovery times when compared to traditional, open incision surgery. In addition, the use of a teleoperational medical system, such as the DA VINCI® Surgical System commercialized by Intuitive Surgical, Inc., Sunnyvale, California, is known. Such teleoperational medical systems may allow a surgeon to operate with intuitive control and increased precision when compared to manual minimally invasive surgeries.

A teleoperational medical system may include one or more instruments that are coupled to one or more robotic arms. If the system is used to perform minimally invasive surgery, the instruments may access the surgical area through one or more small openings in the patient, such as small incisions or natural orifices, such as, for example, the mouth, urethra, or anus. In some cases, rather than having the instrument(s) directly inserted through the opening(s), a cannula or other guide element can be inserted into each opening and the instrument can be inserted through the cannula to access the surgical area. An imaging tool such as an endoscope can be used to view the surgical area, and the image captured by the imaging tool can be displayed on an image display to be viewed by the surgeon during a surgery.

It is desirable to provide teleoperational medical systems provide flexibility to the user to tradeoff instrument reach and patient clearance in a straightforward manner which can be safely adjusted at any time intraoperatively. The systems and methods disclosed herein overcome one or more of the deficiencies of the prior art.

SUMMARY

In an exemplary aspect, the present disclosure is directed to a teleoperational medical system for performing a medical procedure in a surgical field. The teleoperational medical system includes a teleoperational assembly having a plurality of motorized surgical arms configured to assist in a surgical procedure. The motorized surgical arms have a motion limit defining a boundary beyond which the surgical arm cannot pass when the surgical arm is attached to a patient. The teleoperational medical system also includes a control system having a surgical threshold limit stored therein. The surgical threshold limit is an edge of a boundary to be potentially travelled by the surgical arm to suitably perform a surgical procedure. The control system is configured to compare the motion limit to the surgical threshold limit and notify an operator via an output device when the threshold limit is outside a range of motion bounded by the motion limit.

In an aspect, the surgical threshold limit is pre-stored in the control system and accessed for comparison to the motion limit based upon at least one of the type of surgery, the location of the surgery in the body, patient body features, and the patient approach. In an aspect, the output device comprises one of a visual display and an auditory noise. In an aspect, the teleoperational assembly comprises an adjustable joint to modify an arm pitch and change the motion limit relative to the surgical threshold limit. In an aspect, the adjustable joint is disposed at a proximal portion of the surgical arm. In an aspect, the teleoperational medical system includes an input device configured to activate a motor to adjust the adjustable joint to modify the configuration of the arm and change the motion limit. In an aspect, the control system is configured to notify the operator via a visual notification on the output device when the threshold limit is outside a range of motion bounded by the motion limit, the control system being configured to automatically remove the notification when the motion limit will no longer prevent the surgical arm from moving toward the surgical threshold limit. In an aspect, the motion limit is an electronic motion limit. In an aspect, the motion limit is defined by physical structure of the arm or physical capability of the arm that prevents movement beyond the motion limit.

In another exemplary aspect, the present disclosure is directed to a teleoperational medical system for performing a medical procedure in a surgical field that includes a teleoperational assembly having a plurality of motorized surgical arms configured to assist in a surgical procedure. The motorized surgical arms have a motion limit defining a boundary beyond which the surgical arm cannot pass without reconfiguring the arm when the surgical arm is attached to a patient. The teleoperational medical system also includes a control system having a surgical threshold limit stored therein. The surgical threshold limit is an edge of a boundary to be potentially travelled by the surgical arm to suitably perform a surgical procedure. The control system is configured to compare the motion limit to the surgical threshold limit and notify an operator via the output device when the motion limit is within a preset tolerance of the surgical threshold limit.

In an aspect, the preset tolerance includes a tolerance dimension of less than 10 degrees on a first side of the surgical threshold limit and a tolerance dimension greater than zero on a second side of the surgical threshold, such that the control system notifies the operator when the motion limit is within 10 degrees of the first side the surgical threshold limit or when the motion limit is greater than zero degrees on the second side of the surgical threshold. In an aspect, the preset tolerance includes a tolerance dimension of less than 10 degrees such that the control system notifies the operator when the motion limit is within 10 degrees of the surgical threshold limit. In an aspect, the control system comprises an output device comprising one of a display and a speaker, the control system being configured to notify the operator via the output device when the motion limit is within the preset tolerance of the surgical threshold limit. In an aspect, the control system comprises a plurality of pre-stored surgical threshold limits, each of the plurality of pre-stored surgical threshold limits being associated with a particular type of surgery, wherein the control system selects one of the plurality of pre-stored surgical threshold limits for comparison with the motion limit based on the type of surgery to be performed. In an aspect, the teleoperational assembly comprises an adjustable joint to modify the configuration of the arm and change the motion limit relative to the surgical threshold limit. In an aspect, the adjustable joint is disposed at a proximal portion of the surgical arm. In an aspect, the teleoperational medical system further comprises an input device configured to activate a motor to adjust the adjustable joint to modify the configuration or the arm and change the motion limit.

In yet another exemplary aspect, the present disclosure is directed to a method of operating a teleoperational medical system. The method includes comparing a stored surgical threshold limit to a motion limit, the stored surgical threshold limit being a boundary to be potentially travelled to by a surgical arm to suitably perform a surgical procedure. The motion limit is a boundary beyond which the surgical arm cannot pass when the surgical arm is attached to a patient. The method also includes notifying an operator via the output device when the motion limit might inhibit the surgical arm from moving toward the surgical threshold limit.

In an aspect, notifying an operator when the motion limit might potentially inhibit the surgical arm from moving toward the surgical threshold limit includes notifying the operator when the surgical threshold limit is within 10 degrees of the motion limit. In an aspect, the method also includes accessing the surgical threshold limit from a plurality of pre-stored threshold limits based on at least one of a type of surgery, a location of the surgery in the body, patient body features, and a patient approach. In an aspect, notifying the operator via the output device when the motion limit might inhibit the surgical arm from moving only when there is available range of motion in a desired direction.

These and other embodiments are further discussed below with respect to the following figures.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1B illustrates a front elevation view of an exemplary teleoperational assembly according to one embodiment of the present disclosure. FIG. 1C illustrates a side elevation view of an exemplary arm of a teleoperational assembly according to one embodiment of the present disclosure. FIG. 1D illustrates a portion of the exemplary arm of a teleoperational assembly according to one embodiment of the present disclosure. FIG. 1E illustrates a front elevation view of an exemplary operator input system according to one embodiment of the present disclosure.

DETAILED DESCRIPTION

Figure 1A:
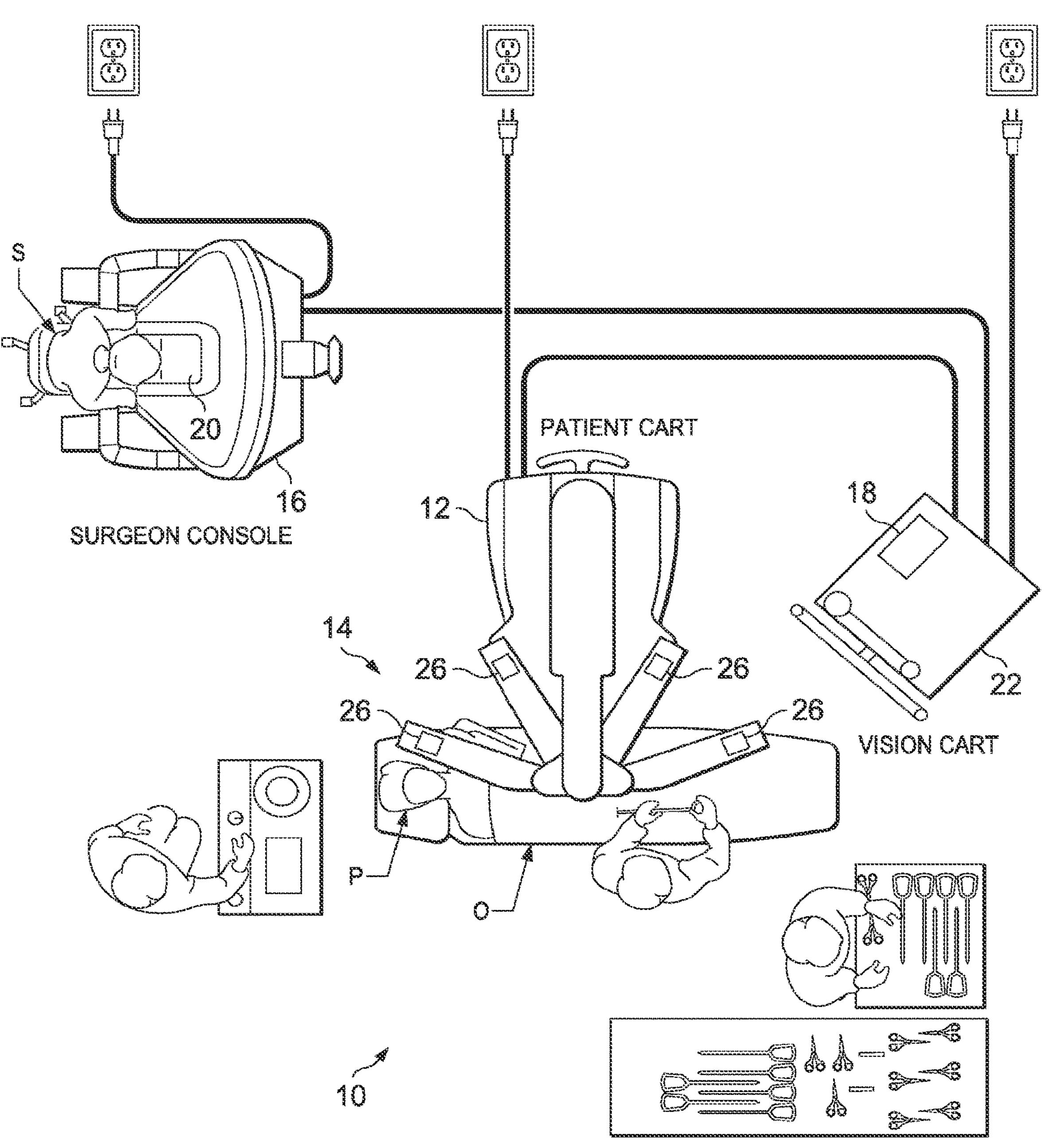
FIG. 1A illustrates an exemplary teleoperational medical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the disclosure.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. The numerous iterations of these combinations will not be described separately. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For simplicity, in some instances the same reference numbers are used throughout the drawings to refer to the same or like parts.

The present disclosure relates generally to an adjustment system that prompts a user to manipulate one or more motorized surgical arms of a teleoperational medical system into an arrangement that permits a user to utilize their effective range of movement. The adjustment system determines whether the original arrangement of the motorized surgical arms has a motion limit, based on the arrangement, that might impact the surgical capability. If the motion limit might impact the surgical capability, the adjustment system prompts the user to make adjustments to the arrangement in order to change the motion limit to a more desirable state.

According to various embodiments, the adjustment system forms a part of a teleoperational system that guides instrument delivery and operation for minimally invasive medical procedures. FIG. 1A of the drawings shows a teleoperational medical system for use in medical procedures including, for example, diagnostic, therapeutic, or surgical procedures. It is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 near or mounted to an operating table O on which a patient P is positioned. The teleoperational assembly 12 may be referred to as a patient-side manipulator (PSM). A medical instrument system 14 is operably coupled to and forms a part of the teleoperational assembly 12. An operator input system 16 allows a surgeon or other type of clinician S to view images of or representing the surgical site and to control the operation of the medical instrument system 14. The operator input system 16 may be referred to as a master or surgeon's console. One example of a teleoperational medical system that can be used to implement the systems and techniques described in this disclosure is a da Vinci® Surgical System manufactured by Intuitive Surgical, Inc. of Sunnyvale, California.

The teleoperational assembly 12 and its medical instrument system 14 may include a kinematic structure of one or more non-servo controlled links (e.g., one or more links that may be manually positioned and locked in place, generally referred to as a set-up structure) and a teleoperational manipulator, such as an arm. (See, e.g., FIG. 1C). The teleoperational assembly 12 includes a plurality of motors that drive inputs on the medical instrument system 14. These motors move in response to commands from a control system 22. It is worth noting that much of the control system may reside within or a part of any of multiple components of the teleoperational medical system 10, including within the teleoperational assembly 12. This allows many of the features to be supported during setup or transport when not connected to the other system components. The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument. The teleoperational assembly 12 may be configured and arranged to sense, such as detect, calculate, or otherwise determine the position of each motor and/or each arm. The teleoperational assembly 12 includes a user interface configured to receive information from and convey information to a user. In some embodiments, the user interface is a touchpad interface that may present information to the user during at least a portion of the surgical process. The teleoperational assembly 12 includes elements 26, such as sensors, switches, encoders, and/or other components that sense the arrangement of components of the teleoperational assembly. The arrangement may include the presence or absence of components as provided in the examples below or may include the physical relative position of components. The control system 22 is operatively linked to the touchpad, sensors, motors, actuators, encoders, hydraulic flow systems, and other components of the teleoperational assembly 12, the operator input system 16, and to an image capture system 18. The image capture system 18 includes an image capture device, such as an endoscope that may be carried on the medical instrument system 14 of the teleoperational assembly 12, and related image processing hardware and software.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. More specifically, in response to the surgeon's input commands, the control system 22 effects servomechanical movement of the medical instrument system 14. The control device(s) may include one or more of any number of a variety of input devices, such as hand grips, joysticks, trackballs, data gloves, trigger-guns, hand-operated controllers, foot-operated controllers, voice recognition devices, touchscreens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The system operator sees images, captured by the image capture system 18, presented for viewing on a display system 20 operatively coupled to or incorporated into the operator input system 16. The display system 20 displays an image or representation of the surgical site and medical instrument system(s) 14 as generated by sub-systems of the image capture system 18. The display system 20 and the operator input system 16 may be oriented so the operator can control the medical instrument system 14 and the operator input system 16 with the perception of telepresence. The display system 20 may include multiple displays such as separate right and left displays for presenting separate images to each eye of the operator, thus allowing the operator to view stereo images.

Alternatively or additionally, display system 20 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including, e.g., time based or velocity based information) images and associated image data sets for reproducing the images.

The control system 22 includes at least one memory and at least one processor (not shown), and typically a plurality of processors, for effecting control between the teleoperational system 12, medical instrument system 14, the operator input system 16, the image capture system 18, and the display system 20. The control system 22 also includes programmed instructions (e.g., a computer-readable medium storing the instructions) to implement some or all of the methods described in accordance with aspects disclosed herein. While control system 22 is shown as a single contained element in FIG. 1, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 22 supports wireless communication protocols such as Bluetooth, IrDA, HomeRF, IEEE 802.11, DECT, and Wireless Telemetry.

The control system 22 also includes a user interface that is configured to receive information from and convey information to a user. In the embodiments described herein, the user interface is a touchscreen monitor that may present notifications, such as alerts, prompts, suggestions, and status updates during the surgical process. In some embodiments, the touchscreen monitor is disposed in a position in the operating room where it can be easily seen as a user sets up or works with the teleoperational assembly 12. This may be within a sterile zone of the system. In contrast, the touchpad on the teleoperational assembly 12 may be disposed at a location outside the sterile zone, and may be accessed by a non-sterile person. In another embodiment, both the touchpad and the touchscreen monitor are in the sterile zone. While described as a touchscreen monitor, other embodiments include other user interfaces, including one or monitors or display screens, a keyboard, a computer mouse, rollers, buttons, knobs, and other user interfaces.

The adjustment system disclosed herein may be one or more computer programs executed on the control system 22 for determining whether a motion limit of the arm or a component of the arm may interfere with the surgical process when using the teleoperational assembly 12. In some embodiments, the adjustment system is executed on any of a wide variety of centralized or distributed data processing architectures. It may also be implemented as a number of separate programs or subroutines, or may be integrated into a number of other aspects of the teleoperational systems described herein.

In some embodiments, the control system 22 may include one or more servo controllers that receive force and/or torque feedback from the teleoperational assembly 12. Responsive to the feedback, the servo controllers transmit signals to the operator input system 16. The servo controller(s) may also transmit signals instructing teleoperational assembly 12 to move the medical instrument system(s) 14 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, eye tracking systems, fluid management systems such as irrigation systems and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 1B:
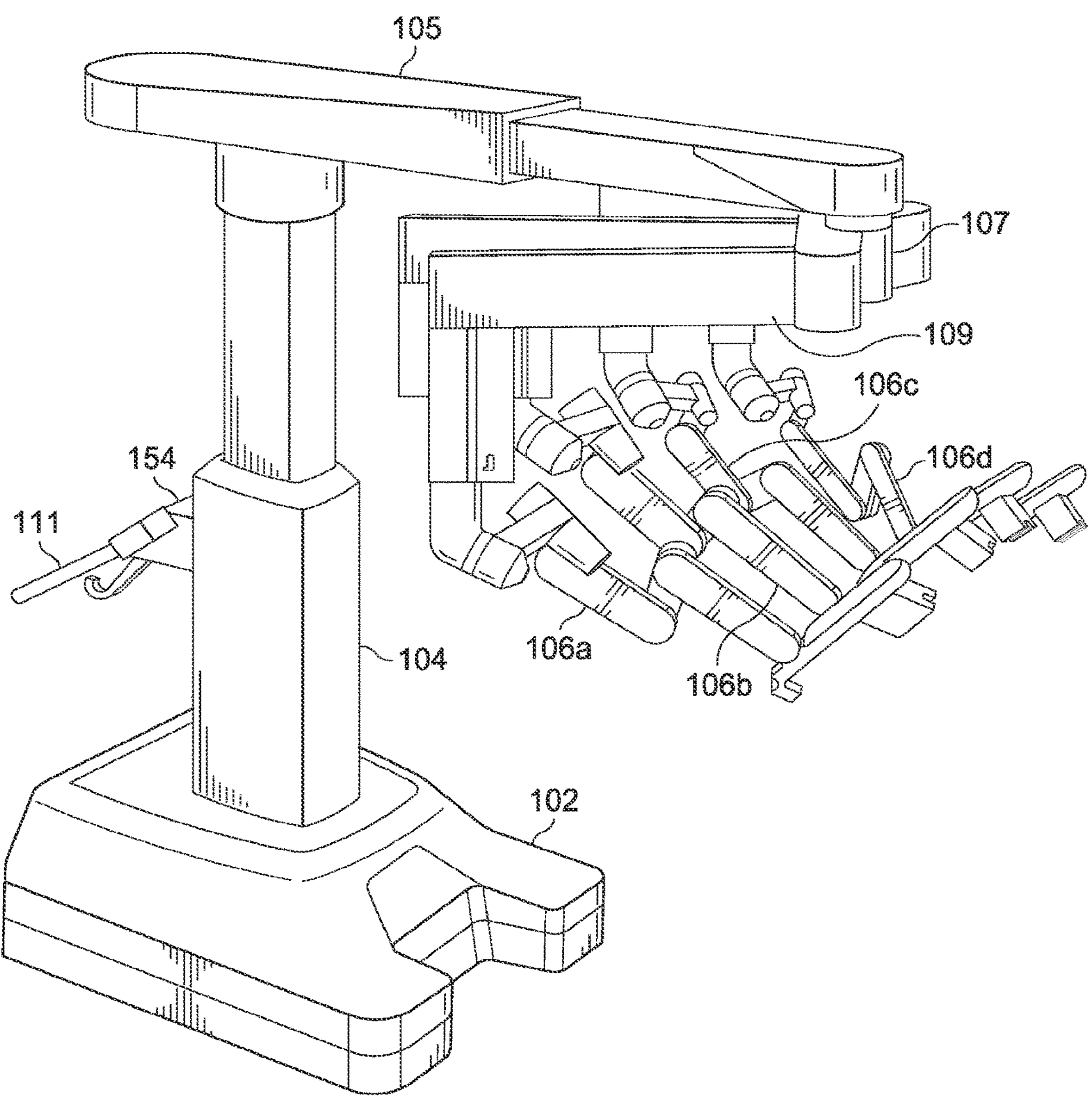
FIGS. 1B, 1C, 1D, 1E, and IF illustrate exemplary components of a teleoperational medical system according to various embodiments of the present disclosure. In particular.

FIG. 1B shows an exemplary teleoperational assembly 100 (e.g., the teleoperational assembly 12 shown in FIG. 1A) according to one embodiment. The assembly 100 includes a base 102 that rests on the floor, a telescoping support column 104 that is mounted on the base 102, a telescoping boom 105 that extends from the support column 104, a platform portion as an orienting platform 107 with support beams 109, and several arms 106 that support surgical tools (including portions of the image capture system 18). As shown in FIG. 1B, arms 106*a*, 106*b*, 106*c*, 106*d* are instrument arms that support and move the surgical instruments used to manipulate tissue. One of these arms 106 may be designated as a camera arm that supports and moves an endoscope.

Figure 1C:
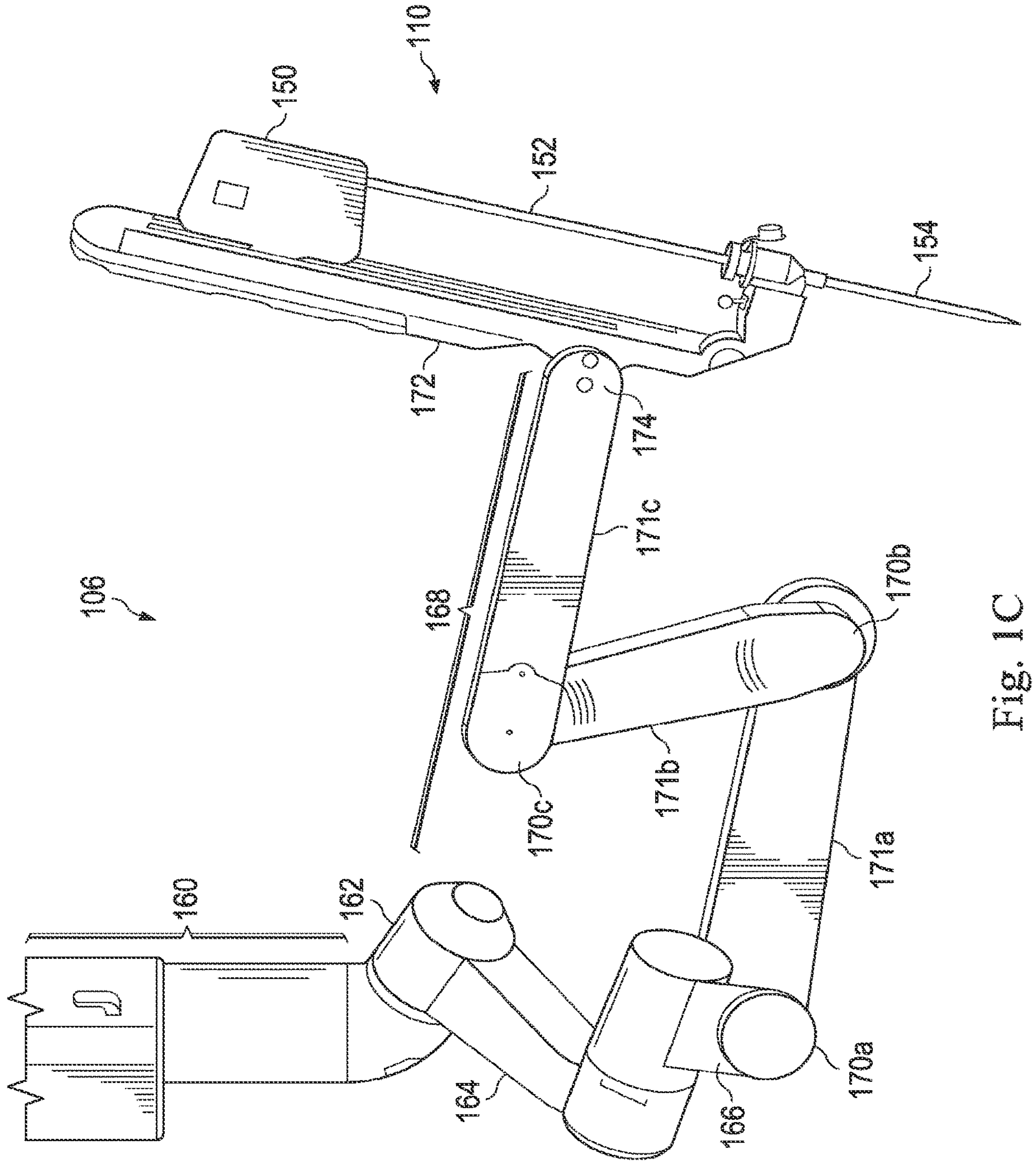

FIG. 1C shows one of the arms 106 with an interchangeable surgical instrument 110 mounted thereon. Depending on the embodiment, the surgical instrument 110 includes an instrument carriage 150, and an instrument shaft 152 extending through a cannula 154. The instrument shaft 152 may form any instrument type intended to interface with the patient during the surgical procedure. In some embodiments, the surgical instrument 110 includes an endoscope as a camera mounted on the arm 106. The endoscope may be a stereo endoscope for capturing stereo images of the surgical site and providing the separate stereo images to the display system 20. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

The instrument carriage 150 may advance and retract the instrument shaft 152 through the cannula 154. In some embodiments, the cannula 154 mounts to a portion of the arm 106 that fixes the surgical instrument 110 with respect to the cannula 154. In some embodiments, portions of each of the instrument arms 106 can be adjustable by personnel in the operating room in order to position the instrument with respect to a patient. Other portions of the arms 106 may be actuated and controlled by the operator at an operator input system 120 (as shown in FIG. 1E). The surgical instrument 110 associated with each arm 106 may also be controlled by the operator at the operator input system 120.

For explanation only, the end having the instrument 110 affixed thereon will be referenced herein as the distal end of the arm 106, and the opposing end having the vertical setup will be referred to as the proximal end. In more detail, the arm 106 includes a vertical setup 160 connected via a setup joint 162 to a distal-most setup link 164. A rotational joint

165 connects the distal-most setup link 162 to the vertical setup 160. A yaw joint 166 connects the distal-most setup link 162 to a parallelogram pitch mechanism 168. The parallelogram pitch mechanism 164 includes a plurality of pitch joints 170*a*, 170*b*, 170*c* connected by pitch struts 171*a*, 171*b*, and 171*c*, enabling it move. A spar 172 connects to the parallelogram pitch mechanism 164 at a spar joint 174. Each of the setup joint 162, the yaw joint 166, the pitch joints 170*a*, 170*b*, 170*c*, and the spar joint 174 are controlled by motors, referenced herein as a setup joint motor, a yaw joint motor, pitch joint motors, and a spar joint motor. Accordingly, the arm 106 is configured to move in a completely motorized fashion. In this embodiment, the motors are under the control of the control system 22 and may be operated in coordination with motors of the other arms to take desired poses that may assist with draping, advancing over a patient, docking to surgical instruments, or storage, among others. In addition, encoders and sensors associated with each motor provide feedback to the control system 22 so that the control system senses or detects the position, status, and setup of the arm 106. In some embodiments, the spar 172 or the instrument carriage 150 includes sensors that detect the presence of surgical drapes on the arms 106. Other elements of the arm 106 may also include sensors that detect the presence of surgical drapes.

Figure 1D:
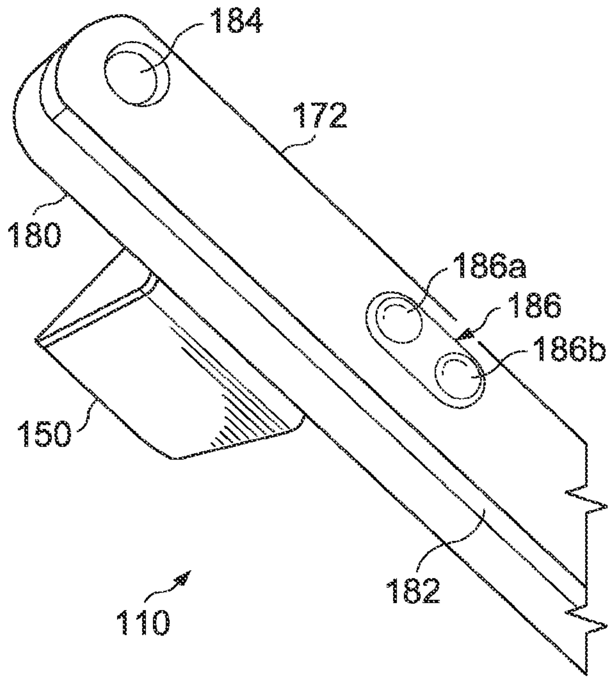
Figure 1E:
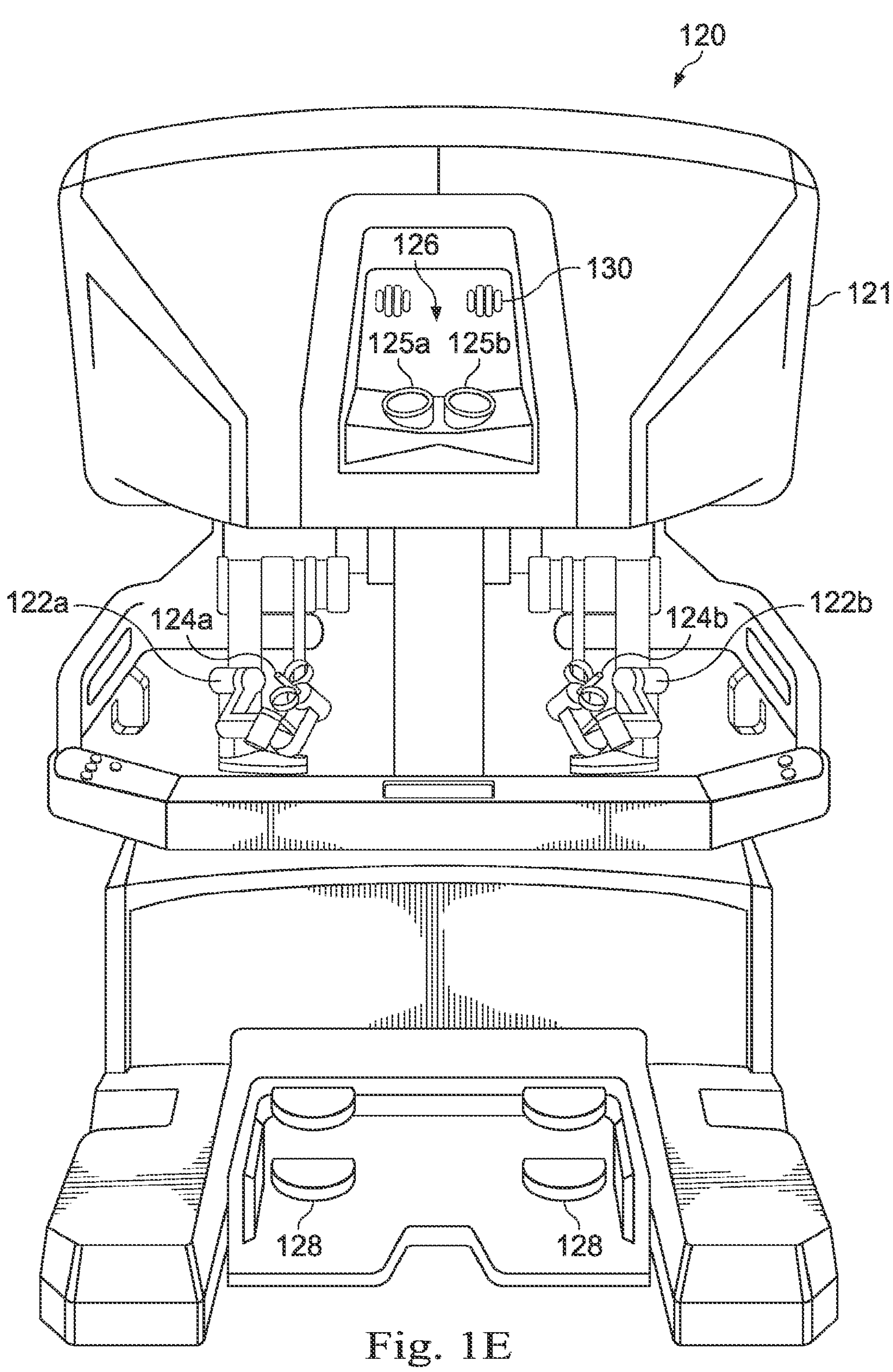

FIG. 1D shows a portion of the spar 172. It includes a distal side 180 and a proximal side 182. In this embodiment, the instrument carriage 150 of the surgical instrument 110 attaches to the distal side 180. The proximal side 182 includes input devices, shown here as a clutch button 184 and clearance buttons 186. The clearance buttons 186 in this embodiment are arranged to allow a user to manually adjust pitch setup angle of the arm 106 by controlling whether the arm is positioned at a steep or shallow angle. In the embodiment disclosed herein, the clearance buttons 186 are a rocker switch forming an "up" button 186*a* and a "down" button 186*b*. These buttons 186 activate a motor that rotates the distal-most setup link 164 relative to the vertical setup 162. In so doing, the pitch setup angle of the arm 106 may be adjusted up or down. The axis of setup joint 162 intersects with the remote center of the manipulator. Thus, the pitch setup angle of the arm 106 can be adjusted without translating the remote center, thereby enabling safe intraoperative adjustment of the pitch setup angle with a cannula connected.

Returning to FIG. 1B, the teleoperational assembly 100 also includes a helm 111 on the support column 104 with a user interface for controlling the setup and operation. In some embodiments, the user interface is a touchpad 154 capable of accepting user inputs and providing graphical, textual, auditory, or other feedback. The touchpad 154 provides features for teleoperational assembly 100 activities such as preparation for draping, docking, or stowing to help the user minimize the space it takes up in the OR. The touchpad 154 also provides a means for system fault notification and recovery. In some embodiments, the touchpad 154 is disposed along the support column 104 and is configured to be viewed by a user in the operating room. In other embodiments, the touchpad or other user interface is disposed elsewhere. The touchpad 154 in this embodiment is configured to display informational data relating to status of the teleoperational assembly 100, information relating to particular surgical procedures, and information relating to the overall teleoperational medical system 10. In some embodiments, the touchpad 154 is a touchpad display interface that presents information and accepts user inputs. As such, a user may input control instructions, including setup instructions, at the touchpad.

FIG. 1E is a front elevation view of an operator input system 120 (e.g., the operator input system 16 shown in FIG. 1A). The operator input system 120 includes a console 121 equipped with left and right multiple degree-of-freedom (DOF) control interfaces 122*a* and 122*b*, which are kinematic chains that are used to control the surgical instruments 110 including the endoscope. The surgeon grasps a pincher assembly 124*a*, 124*b* on each of control interfaces 122, typically with the thumb and forefinger, and can move the pincher assembly to various positions and orientations. When a tool control mode is selected, each of control interfaces 122 is configured to control a corresponding surgical instrument and instrument arm 106. For example, a left control interface 122*a* may be coupled to control the instrument arm 106*a* and its associated surgical instrument 110, and a right control interface 122*b* may be coupled to the control instrument arm 106*b* and its associated surgical instrument 110. If the third instrument arm 106*c* is used during a surgical procedure and is positioned on the left side, then left control interface 122*a* can be switched from controlling the arm 106*a* and its associated surgical instrument 110 to controlling the arm 106*c* and its associated surgical instrument 110. Likewise, if the third instrument arm 106*c* is used during a surgical procedure and is positioned on the right side, then the right control interface 122*a* can be switched from controlling the arm 106*b* and its associated surgical instrument 110 to controlling the arm 106*c* and its associated surgical instrument 110. In some instances, control assignments between the control interfaces 122*a*, 122*b* and combination of arm 106*a*/surgical instrument and combination of arm 106*b*/surgical instrument may also be exchanged. This may be done, for example, if the endoscope is rolled 180 degrees, so that the instrument moving in the endoscope's field of view appears to be on the same side as the control interface the surgeon is moving. The pincher assembly is typically used to operate a jawed surgical end effector (e.g., scissors, grasping retractor, and the like) at the distal end of a surgical instrument 110.

Additional controls are provided with foot pedals 128. Each of foot pedals 128 can activate certain functionality on the selected one of instruments 110. For example, foot pedals 128 can activate a drill or a cautery tool or may operate irrigation, suction, or other functions. Multiple instruments can be activated by depressing multiple ones of pedals 128. Certain functionality of instruments 110 may be activated by other controls.

The surgeon's console 120 also includes a stereo image viewer system 126 (e.g., the display system 20 shown in FIG. 1A). Stereo image viewer system 126 includes a left eyepiece 125*a* and a right eyepiece 125*b*, so that the surgeon may view left and right stereo images using the surgeon's left and right eyes respectively inside the stereo image viewer system 126. Left side and right side images captured by an endoscope are outputted on corresponding left and right image displays, which the surgeon perceives as a three-dimensional image on a display system (e.g., the display system 20 shown in FIG. 1A). In an advantageous configuration, the control interfaces 122 are positioned below stereo image viewer system 126 so that the images of the surgical tools shown in the display appear to be located near the surgeon's hands below the display. This feature allows the surgeon to intuitively control the various surgical instruments in the three-dimensional display as if watching the hands directly. Accordingly, the servo control of the associated instrument arm and instrument is based on the endoscopic image reference frame.

The endoscopic image reference frame is also used if the control interfaces 122 are switched to a camera control mode. In some cases, if the camera control mode is selected, the surgeon may move the distal end of endoscope by moving one or both of the control interfaces 122 together. The surgeon may then intuitively move (e.g., pan, tilt, zoom) the displayed stereoscopic image by moving the control interfaces 122 as if holding the image in his or her hands.

As is further shown in FIG. 1E, a headrest 130 is positioned above stereo image viewer system 126. As the surgeon is looking through stereo image viewer system 126, the surgeon's forehead is positioned against headrest 130. In some embodiments of the present disclosure, manipulation of endoscope or other surgical instruments can be achieved through manipulation of headrest 130 instead of utilization of the control interfaces 122.

Figure 1F:
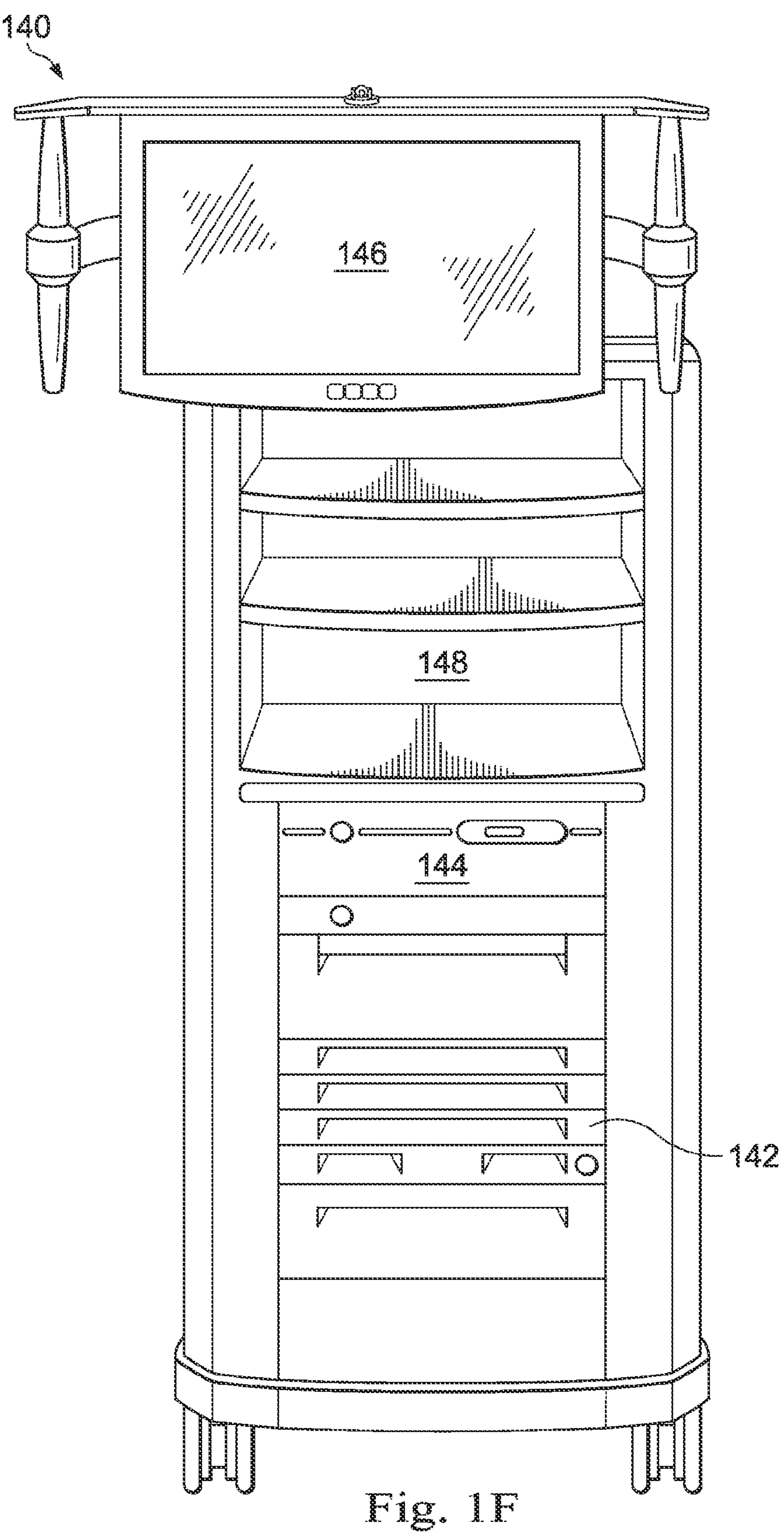
FIG. 1F illustrates a front view of an exemplary vision cart component according to one embodiment of the present disclosure.

FIG. 1F is a front view of a vision cart component 140 of a medical system. For example, in one embodiment, the vision cart component 140 is part of the medical system 10 shown in FIG. 1A. The vision cart 140 can house the medical system's central electronic data processing unit 142 (e.g., all or portions of control system 22 shown in FIG. 1A) and vision equipment 144 (e.g., portions of the image capture system 18 shown in FIG. 1A). The central electronic data processing unit 142 includes much of the data processing used to operate the medical system. In various implementations, however, the electronic data processing may be distributed in the surgeon console 120 and teleoperational assembly 100. The vision equipment 144 may include camera control units for the left and right image capture functions of the endoscope. The vision equipment 144 may also include illumination equipment (e.g., a Xenon lamp) that provides illumination for imaging the surgical site. As shown in FIG. 1F, the vision cart 140 includes an optional touchscreen monitor 146 (for example a 24-inch monitor), which may be mounted elsewhere, such as on the assembly 100 or on a patient side cart. Speakers may also be mounted to the patient side cart or at other locations about the teleoperational medical system. The vision cart 140 further includes space 148 for optional auxiliary surgical equipment, such as electrosurgical units, insufflators, suction irrigation instruments, or third-party cautery equipment. The teleoperational assembly 100 and the surgeon's console 120 are coupled, for example, via optical fiber communications links to the vision cart 140 so that the three components together act as a single teleoperated minimally invasive medical system that provides an intuitive telepresence for the surgeon.

The touchscreen monitor 146 may form a user interface that provides notifications, such as alerts, prompts, and status during the surgical process. While a touchscreen monitor is shown, it is worth noting that other types of user interfaces may be used, including those described above with reference to the touchpad 154. In some embodiments the user interface is merely a display that does not receive user inputs.

Note that in some embodiments, some or all of the assembly 100 of the teleoperated medical system can be implemented in a virtual (simulated) environment, wherein some or all of the image seen by the surgeon at the surgeon's console 120 can be synthetic images of instruments and/or anatomy. In some embodiments, such synthetic imagery can be provided by the vision cart component 140 and/or directly generated at the surgeon's console 120 (e.g., via a simulation module).

Figure 2A:
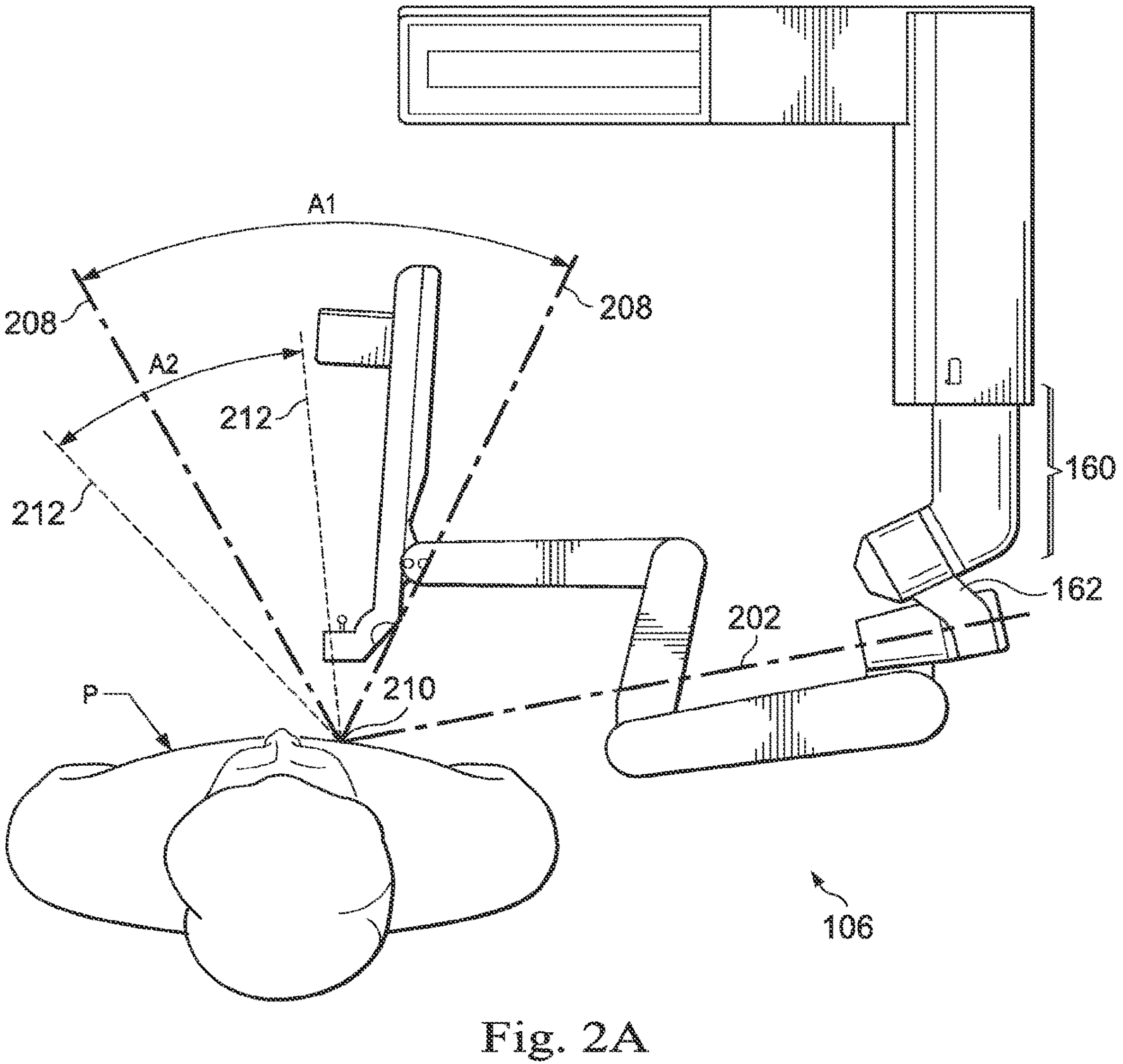
FIGS. 2A and 2B illustrate the exemplary arm of FIG. 1C in orientations having a shallower pitch and a steeper pitch according to embodiments of the present disclosure.
Figure 2B:
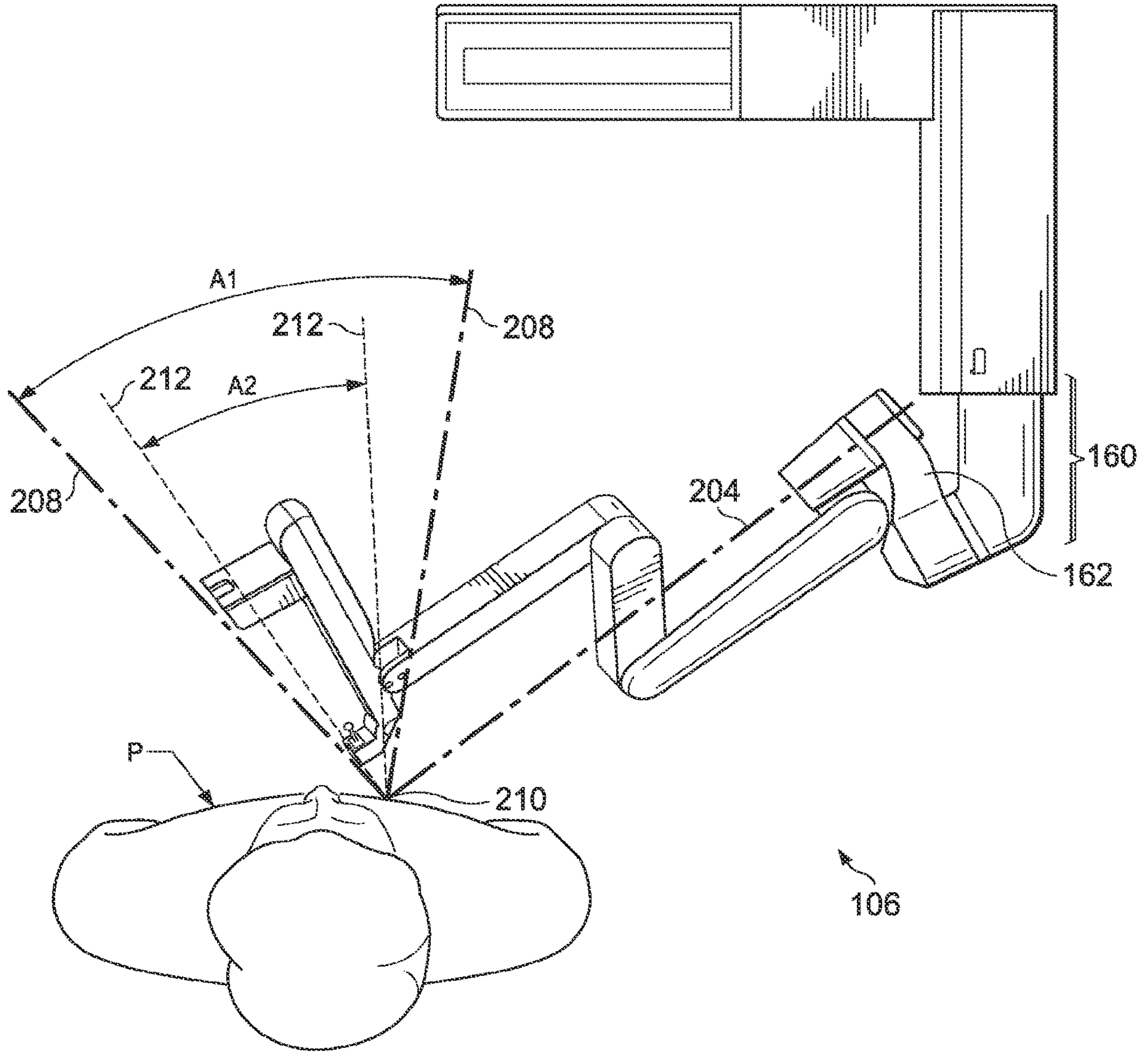

FIGS. 2A and 2B show an arm 106 in arrangements having different pitches extending above a patient P lying prone. The pitch of the arm 106 is the angle of the arm 106 measured in a relatively vertical plane. The pitch can be measured through the yaw joint 166 as shown in FIGS. 2A and 2B or may be measured elsewhere. For example, it may be measured along the general overall angle of the arm 106 instead of through a specific joint or linkage. Depending on the angle of the arm 106, the pitch may be steeper or higher, as in FIG. 2B, or may be lower or shallower as in FIG. 2A. FIG. 2A shows the arm 106 at a shallow angle, as represented by the reference line 202, extending through the yaw joint 166. The lines 208 in FIG. 2A represent motion limits 208 of the arm 106 about an anatomical orifice 210 of the patient P, The angle A1 between the motion limits 208 defines the range or motion that may be taken by the arm 106 without removing the arm from the patient. As can be seen, in the shallow angle arrangement shown in FIG. 2A, the motion limits 208 are nearly at an angle of about 20 degrees from vertical in both the distal and the proximal directions, providing a full range of motion represented by the angle A1 of about 40 degrees. The motion limits 208 are typically established by the mechanical limitations of each link, the motors at each joint, or other physical limitations. In some embodiments however, the motion limits 208 are established via electronic control or other means. The range of motion of 40 degrees is merely an example of the motion range, and the actual motion range may be higher or lower and may be determined by the physical makeup of the arm and/or electronic limits.

Still referring to FIG. 2A, the dashed lines in FIG. 2A represent surgical threshold limits 212 about the anatomical orifice 210 to the patient P. The surgical threshold limits 212 are the angular limits defining an access range in which the surgical procedure can be properly performed. That is, they define the boundary lines in which the target tissue can be properly accessed and treated during the surgical procedure. The exemplary surgical threshold limits 212 in FIG. 2A are shown as having an angle from vertical of about 5 degrees in the distal direction to about 30 degrees in the distal direction. The angle A2 between these surgical threshold limits 212 defines the threshold surgical range in which the surgical instruments 110 may be manipulated to properly carry out the surgical procedure. The surgical threshold limits 212 may be dependent on the type of surgery, the location of the surgery in the body and may be influenced by adjacent organs, tissue, or other patient body features. It may also be influenced by the patient approach or other factors relating to the structure of the teleoperational assembly 100.

FIG. 2B shows the arm 106 arranged at a steep angle or high pitch as represented by the reference line 204. Here, since the patient P is still lying prone on his back, the surgical threshold limits 212 are unchanged. However, the motion limits 208, due the steeper angle or greater pitch when compared to the shallow angle or lower pitch in FIG. 2A, are also changed. Here, the motion limits 208 may be measured from vertical to be about 10 degrees in the proximal direction and about 30 degrees in the distal direction. Some arm embodiments have a pitch range of motion of +/−75 degrees. The pitch distal-most setup link 162 determines the pitch angle of the arm 106 with respect to the base 102 and is able to rotate the arm workspace approximately +/−15 degrees.

In some scenarios, the motion limits 208 and the threshold limits 212 may coincide, while in other scenarios, they do not. As can be seen in FIG. 2A, the more distal threshold limit 212 is outside of the range of the motion limit 208. Therefore, if a surgical procedure where to occur with the arrangement in FIG. 2A, with the exemplary surgical threshold limit shown and the exemplary motion limit shown, it is possible that the motion limit would adversely impact the ability of the arm to perform the surgical procedure since the arm cannot move within the full range of motion available for the surgical threshold limits 212. FIG. 2B, however, shows the surgical threshold limits 212 entirely contained within the range of motion A1 defined by the motion limits 208. Therefore, the arm 106 is entirely capable of performing the surgical procedure without being limited by the movement capabilities of the arm 106. Accordingly, depending upon the surgical procedure and depending upon the height and size of the patient, the motion limits may affect the ability to carry out an unrestricted surgical procedure.

Because the arm motion limits are affected by the pitch of the arm (e.g., whether the arm is at a shallow or steep angle), the teleoperational medical system 10 is configured to recognize when the arm pitch is set at an angle that may cause the motion limits to impact the surgical capability for a particular surgery or patient. At the same time, it is important that the arms 106 be positioned in a manner that allows the arms to be sufficiently high to be introduced over the patient without impacting the patient or any cannulas or other instrumentation that may be associated with the patient.

Accordingly, the adjustment system may balance the need for pitch motion limits that are sufficient to not interfere with a surgical procedure, and the need to have the arm 106 high enough above the patient to permit easy setup over the patient to perform the surgery. The teleoperational medical system 10 disclosed herein identifies out of range conditions and alerts the user to the conditions so that adjustments may be made to the arm 106 to place the surgical thresholds in the motion range of the arm.

Figure 3:
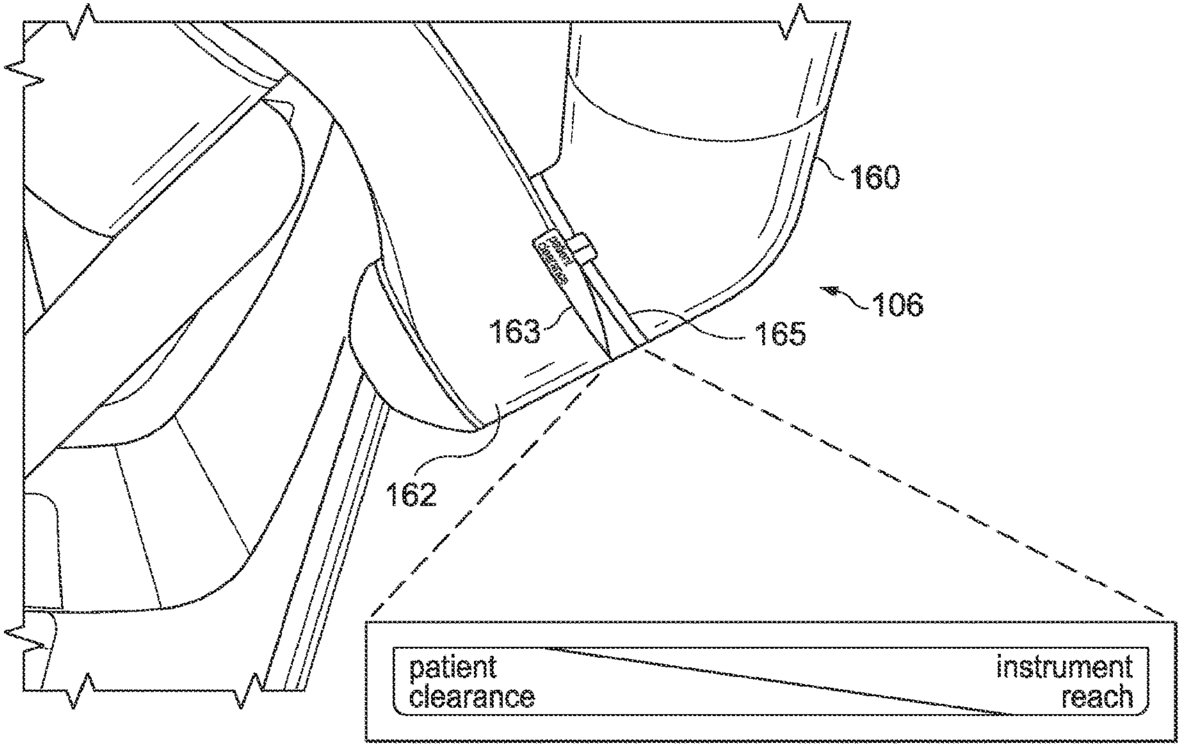
FIG. 3 illustrates an adjustable portion of the exemplary arm of FIG. 1C according to one embodiment of the present disclosure.

FIG. 3 shows the distal-most setup link 162 and a portion of the vertical setup 160. As explained above, rotating the distal-most setup link 162 relative to the vertical setup 160 changes the pitch of the arm 106. As the distal-most setup link 162 rotates in one direction, the arm pitch angle decreases or becomes shallower. This is represented by the decal 163 disposed at the rotational joint 165 between the distal-most setup link 162 and the vertical setup 160. The decal 163 shows that as the distal-most setup link 162 rotates one direction, the patient clearance increases and the instrument reach decreases. At the same time, this change in pitch changes the position of the motion limits relative to a patient or relative to a global coordinate system. Likewise, as the distal-most setup link 162 rotates in the opposing direction, the arm pitch angle increases or becomes steeper. As such, the resulting patient clearance decreases, and the instrument reach increases. This also changes the pitch. Accordingly, merely by rotating the distal-most setup link, the arm pitch changes, which directly impacts the motion limits of the arm.

In some embodiments, the rotational angle of the distal-most setup link 162 is controlled by pressing the clearance buttons 168 on the spar 172, as shown in FIG. 1D. Because the buttons are disposed on the spar 172, the user pressing the buttons is typically also standing directly adjacent the arm 106 and can visually monitor the effect of the changing pitch to ensure that the arm 106 does not contact the patient or any other critical element for the surgery.

In some embodiments, if during the surgical procedure, the adjustment system determines that the motion range may have an impact on the surgical capabilities of the arm 106, the adjustment system notifies the user to adjust the pitch of the arm 106. In some embodiments, the notification may be displayed as a prompt or message on the touchscreen monitor 146 of the vision cart 140. In some embodiments, the notification may be in form of an auditory signal or alert from a speaker, an alarm light on the arm or elsewhere about the teleoperational medical system 10.

Figure 4:
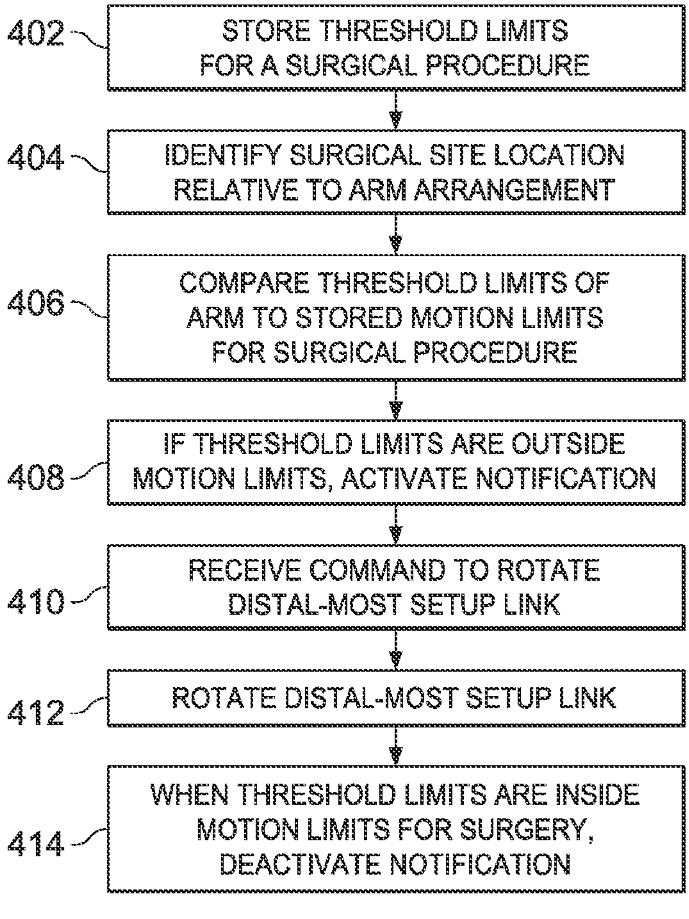
FIG. 4 illustrates an exemplary method for performing a method according to an aspect of the present disclosure.

An exemplary method of identifying the pitch and providing an alert to the user is described with reference to the flow chart in FIG. 4. FIG. 4 starts at 402 with a step of storing threshold limits for a surgical procedure in the medical system's central electronic data processing unit 142. In some embodiments, the threshold limits may be surgical procedure dependent. For example, a surgical procedure to access the thoracic region of the patient may require a different set of threshold limits than a surgical procedure to access a pelvic area. As another example, a surgical procedure having a single access site into the patient may have a different set of threshold limits than a surgical procedure having multiple access sites into the patient. Some embodiments also consider the approach to the patient. For example, whether the teleoperational assembly 100 is disposed on the right side, the left side, or at the legs of the patient. In some examples, the threshold limits are defined by the surgical procedures, anatomical access, or the limitations of cannulas or instruments, for example. In other embodiments, the threshold limits may be determined generally as recommended threshold limits for all procedures. Other factors and consideration also may be used to determine the threshold limits. The threshold limits may be pre-stored during manufacturing of the teleoperational medical system 10, or may be entered at the surgical site or customized for a particular surgeon of group of surgeons.

At 404, the location of the surgical site is identified relative to the arrangement of the arm 106. This may be considered a targeting process that ensures that the teleoperational assembly 100 is well-centered and properly aligned to the surgical site prior to installing instruments. In some embodiments, this process includes pointing the endoscope in the direction of the anatomy of interest and pressing and holding a targeting button, located on the endoscope body. In response, the teleoperational assembly 100 may adjust the boom height to provide clearance above the arms 106 and the patient P (to minimize the likelihood that users inadvertently touch the boom with instruments while installing or uninstalling them from the arms throughout the process). It may also rotate the boom so that the principal working direction is aligned with the arm being used to perform the targeting.

As discussed with reference to FIGS. 2A and 2B, the arrangement of the boom and arms impacts the pitch angle, and therefore the position of the motion limits of the each arm. Steep angles or high pitch are generally preferable when it is advantageous to make more room under the arm for the patient or for other OR equipment such as stirrups, etc., whereas shallow angles are generally better when there is more than adequate patient clearance and it is important to achieve the maximum working range of motion for the arm. Thus, while the motion limits of the arm 106 may be adjusted by repositioning the arm, the surgical threshold limits for the patient are maintained relatively constant in place to avoid repositioning the patient. Of course, if the patient were moved, the threshold limits would move with the patient.

At 406, the central electronic data processing unit 142 compares the motion limits of the arm 106 at the particular pitch angle to the pre-stored threshold limits. The motion limits may be established by the physical structure of the arm 106, or may be electronic limits established to avoid the mechanical stops of structural components abutting each other. In some embodiments, the threshold limits are considered outside the range of the motion limits if they are sufficiently close to the motion limits to create a chance of preventing the arm from moving to the threshold limit. Accordingly, some embodiments have a tolerance level about the threshold limits, and if the motion limits are within the tolerance around the threshold limits, even if not outside the limits, then the adjustment system responds as though the threshold limits are beyond the boundaries of the motion limits. In some examples, if the motion limits are within ten degrees of the threshold limits, then the threshold limits are considered to be outside the motion limits. In other embodiments, if the motion limits are within five degrees of the threshold limits, then the threshold limits are considered to be outside the motion limits. In some embodiments, the tolerance is ten degrees on one side of the surgical threshold limit and anything greater than zero on the other side of the surgical threshold. In some embodiments, the tolerance is five degrees on one side of the surgical threshold limit and anything greater than zero on the other side of the surgical threshold. Some embodiments use a one degree tolerance. Such a small tolerance makes it so the user is not distracted by a prompt until they are right at the boundary of the workspace. The user may also feel force feedback resistance on the surgeon console when trying to push into this unreachable workspace. Depending on the embodiment, the prompt to adjust the setup pitch angle will persist while the arm is within this tolerance of its pitch axis limit.

If at 406, the pre-stored threshold limits are within the motion limits, then the surgical procedure should be able to take place without reaching the motion limits, and no modification is necessary. However, at 508 if the pre-stored threshold limits are outside the motion limits, then there is a chance that the arm 106 will be prevented or inhibited from performing at least a portion of the surgical procedure. Therefore, the central electronic data processing unit 142 activates a user notification. This notification is an alert that may be, for example and without limitation, visual or auditory. In some embodiments, the central electronic data processing unit 142 displays a notification on the touchscreen monitor 146 and/or make a warning sound issue a voice instruction. The notification may instruct the user to adjust the distal-most setup link so that the motion limits more fully align with the threshold limits. In other embodiments, the notification may merely warn the user. The notification may also be auditory. For example a recorded voice from a speaker may warn or instruct the user that the arm pitch should be adjusted. In some embodiments, the notification is a one-time alert that warns the user, while in other embodiments, the notification may a persistent alert that continues until the user adjusts the pitch angle of the arm using the distal-most setup link.

At 410, after the notification is activated, the central electronic data processing unit 142 may receive an input at the clearance button 186 to rotate the distal-most setup link 162 and change the arm pitch at 412. In some embodiments, a user enters an input, such as by pressing a button to rotate the distal-most setup link 162. In the example in FIG. 1D, the user may press one of two buttons, with one button 186*a* causing the distal-most setup link 162 to rotate in one direction, and the other button 186*b* causing the distal-most setup link 162 to rotate in the other. For example, when the "up" button is pressed and held, teleoperational assembly 100 moves the arm 106 to a steeper angle to provide more patient clearance. Conversely, when the "down" button is pressed and held, the teleoperational assembly 100 moves the arm 106 to a shallower angle to provide greater instrument reach. In preferred embodiments, adjustment of the patient clearance setting does not affect the position of the instrument tip, if an instrument is installed. This is achieved by using the joints of the arm 106 to compensate for the change in orientation of the setup pitch angle. The arm 106 may be considered to rotate in the nullspace of the instrument tip.

The electronic data processing unit 142 continues to compare the motion limits to the stored threshold limits. At 414, when the electronic data processing unit 142 determines that the threshold limits are within the motion limits for the surgery, the electronic data processing unit 142 automatically turns off or resets the notification. In other embodiments, the user inputs a command to turn off or reset the notification alert.

While the process is described for only a single arm, it should be understood that the process occurs for each arm used in the surgical procedure. In some embodiments, the process is repeated in sequence for each arm to confirm each arm is properly positioned for the surgery. In other embodiments, the process is performed in parallel, so that notifications may be presented for all arms to make the adjustment process more efficient. Other methods and arrangements are also contemplated.

Some embodiments are configured so that the system only prompts a user to adjust the setup pitch angle if there is available range of motion remaining in the desired direction. For example, if the setup pitch angle is already as low as it can go, then the user is not prompted if the manipulator pitch approaches the lower threshold. Likewise, if the setup pitch angle is already at its upper limit and the manipulator pitch is within tolerance of the upper limit, then the user is no longer prompted to raise the setup pitch angle.

In some embodiments, the pitch threshold limits are defined in space which can move with the patient. In another example, the system is configured so that a user may define the pitch threshold by lowering the arm 106 to the minimum permissible patient clearance. The arm then dynamically moves the pitch setup angle as needed to provide an augmented pitch workspace. This is beneficial if the arms are being used to work between extreme pitch forward and pitch back poses. In some aspects, the pitch threshold limits may be dynamically adjusted when repositioning the patient via the operating table controls. For instance, in some embodiments, putting the patient into a steeper trendelenburg pose raises the pitch threshold and reminds the users to adjust the arms for appropriate patient clearance. Moreover, the system dynamically adjusts the pitch setup angle to keep the arm 106 above the moving threshold limit.

It should be recognized that although a range and two boundaries are shown in FIGS. 2A and 2B, one boundary may also be used. For example, some embodiments need not take into account two boundaries because the nature of the surgical device is limited for practical surgical purposes in one direction. Accordingly, the adjustment system may compare a single motion limit to a single threshold limit in the manner discussed herein. In addition, one of ordinary skill will recognize that the angles and ranges shown in and discussed with reference to FIGS. 2A and 2B are exemplary only. The actual motion limits may be dependent on the structure of the arm 106, and the actual threshold limits for any particular surgery may be depending on a number of factors.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A system comprising:

a sensing means for sensing an arrangement of a manipulator assembly, wherein the manipulator assembly comprises an arm having a plurality of links coupled by a plurality of joints, and wherein sensing the arrangement of the manipulator assembly comprises: sensing an arrangement of the arm; and a control means for:

determining a motion limit of the manipulator assembly based on the sensed arrangement of the manipulator assembly by: using at least one position selected from the group consisting of: a position of a joint of the plurality of joints and a position of a link of the plurality of links;

selecting a threshold limit from a plurality of pre-stored threshold limits based on which procedure type is to be performed with the manipulator assembly, the selected threshold limit being associated with a procedure type and defining a limit of a range to be potentially travelled by the manipulator assembly to suitably perform a procedure of the associated procedure type;

comparing the motion limit to the selected threshold limit to determine whether the selected threshold limit is outside a range of motion bounded by the motion limit; and providing a notification indicative of whether the selected threshold limit is outside the range of motion bounded by the motion limit.

2. The system of claim 1, wherein the arm is configured to pivot around a remote center, and wherein the system further comprises:

an adjusting means for adjusting the position of the joint of the plurality of joints to change an arrangement of the arm without translating the remote center, such that the arrangement of the manipulator assembly is modified and the motion limit is changed.

3. The system of claim 2, further comprising:

an input device means for commanding the adjusting means, wherein the input device means is disposed on the arm.

4. The system of claim 1, wherein the procedure is a medical procedure, and wherein the control means is further for:

accessing the selected threshold limit for comparison to the motion limit based upon at least one parameter selected from the group consisting of: a location of the medical procedure in a patient's body, a patient body feature, and a patient approach.

5. The system of claim 1, wherein the control means is further for:

comparing the motion limit to the selected threshold limit as the arrangement of the manipulator assembly is changed; and automatically turning off the notification when the selected threshold limit is within the motion limit.

6. The system of claim 1, wherein providing the notification indicative of whether the selected threshold limit is outside the range of motion bounded by the motion limit comprises:

providing the notification to indicate that the selected threshold limit is outside the range of motion bounded by the motion limit.

7. The system of claim 1, wherein providing the notification indicative of whether the selected threshold limit is outside the range of motion bounded by the motion limit comprises:

providing the notification in response to the motion limit being within a preset tolerance of the threshold limit, wherein the preset tolerance includes unequal dimensions on different sides of the threshold limit.

8. The system of claim 1, wherein the notification instructs a user to adjust the manipulator assembly to increase an alignment between the motion limit and the threshold limit.

9. The system of claim 8, wherein the control means is further for:

providing the notification instructing the user to adjust the manipulator assembly only if the motion limit of the manipulator assembly has remaining an available range of motion.

10. The system of claim 1, further comprising:

means for changing the threshold limit in response to a movement of a patient on which the procedure is performed.

11. A computer-assisted system, comprising:

sensing means for sensing an arrangement of an arm configured to assist in a procedure, the arm having a motion limit defining a boundary beyond which the arm cannot pass; and control means for:

accessing a stored threshold limit from a plurality of pre-stored threshold limits based on at least one parameter selected from the group consisting of: a type of procedure, a location of the procedure, a feature of a body on which the procedure is to be performed, and an approach to the body;

comparing the accessed stored threshold limit to the motion limit, the stored threshold limit being a boundary to be potentially travelled to by the arm to suitably perform a procedure; and providing an operator notification via an output device in response to the comparing indicating that the motion limit might inhibit the arm from moving toward the stored threshold limit.

12. The system of claim 11, wherein the comparing indicates that the motion limit might potentially inhibit the arm from moving toward the stored threshold limit when the stored threshold limit is within 10 degrees of the motion limit.

13. The system of claim 11, wherein the control means is further for:

determining if an available range of motion exists in a direction, wherein the providing the operator notification provides the operator notification only when the available range of motion exists in the direction.

14. The system of claim 11, further comprising:

adjusting means for adjusting a joint of the arm and changing the motion limit relative to the stored threshold limit, wherein the joint is disposed at a proximal portion of the arm.

15. The system of claim 14, further comprising:

input means for commanding the adjusting means, the input means disposed on the arm.

16. The system of claim 15, wherein the joint is a rotary joint that rotates about an axis intersecting a remote center of the arm.

17. The system of claim 11, wherein the control means is further for:

automatically removing the operator notification when the motion limit will no longer prevent the arm from moving toward the stored threshold limit.

18. A system, comprising:

sensing means for sensing an arrangement of an arm, wherein the arrangement of the arm is associated with a motion limit, the motion limit defining a boundary beyond which the arm cannot pass without reconfiguring the arm; and control means for:

pre-storing a plurality of threshold limits, each of the plurality of threshold limits being associated with a type of procedure, each of the plurality of threshold limits being a boundary defining a limit of a range to be potentially travelled by the arm to suitably perform a procedure for the associated type of procedure;

selecting a threshold limit of the plurality of threshold limits for comparison with the motion limit based on the type of procedure to be performed;

comparing the motion limit to the selected threshold limit to determine whether the motion limit is within a preset tolerance of the selected threshold limit; and notifying an operator via an output device in response to the comparing indicating that the motion limit is within a preset tolerance of the selected threshold limit.

19. The system of claim 18, further comprising:

adjusting means for adjusting a joint of the arm and changing the motion limit relative to the selected threshold limit.

20. The system of claim 18, wherein the procedure is a medical procedure, and wherein the control means is further for:

accessing the selected threshold limit for comparison to the motion limit based upon at least one parameter selected from the group consisting of: a location of the procedure in a patient, a body feature of the patient, and an approach of the system toward the patient.

* * * * *